(12) United States Patent
Lutrario et al.

(10) Patent No.: US 8,097,573 B2
(45) Date of Patent: *Jan. 17, 2012

(54) NATURAL PERSONAL CLEANSER COMPOSITIONS

(75) Inventors: Celeste Anne Lutrario, Morrisville, NC (US); Karen Lee Rokitowski, Morrisville, NC (US); Jason Everett Costa, Morrisville, NC (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/018,613

(22) Filed: Feb. 1, 2011

(65) Prior Publication Data

US 2011/0124543 A1     May 26, 2011

Related U.S. Application Data

(62) Division of application No. 12/276,888, filed on Nov. 24, 2008, now Pat. No. 7,902,134.

(51) Int. Cl.
*A61K 7/50*     (2006.01)

(52) U.S. Cl. ........ 510/130; 510/424; 510/428; 510/463; 510/470; 510/499

(58) Field of Classification Search .................. None
See application file for complete search history.

(56) References Cited

U.S. PATENT DOCUMENTS

| | | | |
|---|---|---|---|
| 4,992,476 A | 2/1991 | Geria | |
| 5,063,062 A | 11/1991 | Greenspan et al. | |
| 5,182,105 A | 1/1993 | Takata et al. | |
| 5,360,824 A | 11/1994 | Barker | |
| 5,643,583 A | 7/1997 | Voultoury et al. | |
| 5,958,436 A | 9/1999 | Hahn et al. | |
| 5,997,889 A | 12/1999 | Durr et al. | |
| 6,146,645 A | 11/2000 | Deckers et al. | |
| 6,190,678 B1 * | 2/2001 | Hasenoehrl et al. | 424/401 |
| 6,193,987 B1 | 2/2001 | Harbeck | |
| 6,485,756 B1 | 11/2002 | Aust et al. | |
| 6,497,890 B2 | 12/2002 | Youssefyeh | |
| 6,544,530 B1 | 4/2003 | Friedman | |
| 6,582,710 B2 | 6/2003 | Deckers et al. | |
| 6,596,779 B1 | 7/2003 | Jean-Noel et al. | |
| 6,599,513 B2 | 7/2003 | Deckers et al. | |
| 6,924,256 B2 | 8/2005 | Massaro et al. | |
| 6,967,023 B1 | 11/2005 | Eini et al. | |
| 7,060,306 B2 | 6/2006 | Springstead | |
| 7,101,578 B1 | 9/2006 | Revivo | |
| 7,138,129 B2 | 11/2006 | Cho et al. | |
| 7,179,152 B1 | 2/2007 | Rhoades | |
| 2003/0198654 A1 | 10/2003 | Palazzolo | |
| 2004/0057921 A1 | 3/2004 | Walsh | |
| 2004/0092482 A1 | 5/2004 | Gupta | |
| 2005/0031573 A1 | 2/2005 | Cho et al. | |
| 2005/0058669 A1 | 3/2005 | Krzysik et al. | |
| 2005/0084465 A1 | 4/2005 | Baxter | |
| 2005/0158351 A1 | 7/2005 | Soliman et al. | |
| 2005/0255166 A1 | 11/2005 | Moloney | |
| 2006/0210519 A1 | 9/2006 | Wake et al. | |
| 2007/0071711 A1 | 3/2007 | Vromen | |
| 2007/0141012 A1 | 6/2007 | Cho et al. | |
| 2007/0281033 A1 | 12/2007 | Rochat | |
| 2008/0152722 A1 | 6/2008 | Norburn | |

FOREIGN PATENT DOCUMENTS

| WO | WO0168040 A2 | 9/2001 |
|---|---|---|
| WO | WO2005097059 A1 | 10/2005 |

* cited by examiner

*Primary Examiner* — Necholus Ogden, Jr.
(74) *Attorney, Agent, or Firm* — Ann Lee

(57) ABSTRACT

A moisturizing, personal cleansing composition with a limited number of naturally-derived, naturally processed, generally regarded as safe (GRAS), biodegradable ingredients comprising a plurality of oleosomes, an anionic surfactant, a non-ionic surfactant, a lipoaminoacidic surfactant, and a humectant. The personal cleansing composition optionally contains a fragrance, vitamin, essential oil, thickener, exfoliant, preservative, plant extract and other beneficial naturally-derived, naturally processed, generally regarded as safe (GRAS), biodegradable ingredients such as royal jelly. The moisturizing, personal cleansing composition cleanses and moisturizes as well as or better than commercial compositions containing synthetically derived cleansing and moisturizing agents.

17 Claims, No Drawings

NATURAL PERSONAL CLEANSER COMPOSITIONS

CROSS REFERENCE TO RELATED APPLICATIONS

The present application is a divisional of application Ser. No. 12/276,888, filed Nov. 24, 2008, now U.S. Pat. No. 7,902,134, which is hereby incorporated by reference.

BACKGROUND OF THE INVENTION

1. Field of the Invention

The present invention relates generally to a moisturizing, cleansing composition suitable for topical application for cleansing the human body, for example the skin and hair (i.e., a personal cleansing composition). The composition is produced from a limited number of naturally-derived, naturally-processed, safe, biodegradable ingredients and has good cleansing and moisturizing properties.

2. Description of the Related Art

Personal cleansing compositions have progressed and created a large chemical industry devoted to developing new synthetic surfactants and moisturizers to achieve ever improving moisturizing, personal cleansers for the consumer. There are currently over ten thousand different synthetic chemicals used in personal care products intended for use on human skin. Although these synthetic chemicals have been tested on animals at some stage, they have never been tested for long term health affects either individually or in combination. Even the majority of those that actually have been found to cause an adverse health effect to some members of the population can still be used.

Typical personal cleansing formulations require multiple synthetic ingredients many of which have suspected human health risks as indicated by peer-reviewed third-party scientific literature. For example, the following synthetic ingredients are commonly found in personal cleansing formulations: parabens; chemical sunscreens such as avobezone and oxybenzone; glycols; phthalates; and ethoxylated ingredients such as sodium myreth sulfate, sodium laureth sulfate, PEGs (Polyethylene Glycol) and PPGs (Polypropylene Glycol); ethanolamines such as DEAs (Diethanolamine), MEAs (Monoethanolamine), TEAs (Triethanolamine):; synthetic polymers such as PVPs (polyvinylpyrrolidone) and Acrylates; and formaldehyde donors such as DMDM Hydantoin, Diazolidinyl Urea and methylisothiazonlinone.

In addition to numerous synthetic ingredients, many personal cleansing formulations may have natural ingredients that are synthetically-derived or processed. Processes such as ethoxylation, sulfination or polymerization have the potential to change the chemical make-up of ingredients that start out natural, but may not remain so after processing. These types of processes dilute or change the composition of an ingredient and can involve caustic solvents, impurities and leave residual compounds behind. Natural, ecological processes such as distillation, condensation, extraction, steamed distillation, pressure cooking and hydrolysis are desirable to maximize the purity of natural ingredients.

Because of a desire to use renewable resources and to eliminate contact with potentially harmful synthetic materials, natural-based personal cleansing compositions are gaining increasing interest. Most of these personal cleansing compositions contain only some natural ingredients with the majority of their components being synthetic. One difficulty in formulating all-natural personal cleansing compositions is achieving acceptable consumer performance with a limited number of raw materials. The number of all-natural ingredients available is scarce when compared to the number of highly developed synthetic surfactants, synthetic moisturizers and other synthetic ingredients.

Prior art personal cleansing compositions do not combine effective moisturizing and cleansing properties using only naturally-derived, naturally-processed, safe, biodegradable ingredients. Prior art personal cleansing compositions do not have at least 95% of the components of the product originating from renewable sources found in nature. Moreover, prior art personal cleanser compositions do not have at least 95% of the components derived from natural, ecological processes. It is therefore an object of the present invention to provide a personal cleansing composition that overcomes the disadvantages and shortcomings associated with those of the prior art.

SUMMARY OF THE INVENTION

In accordance with the above objects and those that will be mentioned and will become apparent below, one aspect of the present invention comprises a moisturizing, personal cleansing composition that cleanses and moisturizes keratinous tissue when topically applied to the tissue. The inventive composition comprises a plurality of oleosomes, an anionic surfactant, a non-ionic surfactant, a lipoaminoacidic surfactant, and a humectant. The oleosomes, anionic surfactant, non-ionic surfactant, lipoaminoacidic surfactant, and humectant are all naturally-derived, naturally-processed, safe and biodegradable.

Another aspect of the present invention comprises a method of cleansing and moisturizing keratinous tissue by topically applying a composition that comprises the following naturally-derived, naturally-processed, safe and biodegradable components comprising a plurality of oleosomes, an anionic surfactant, a non-ionic surfactant, a lipoaminoacidic surfactant, and a humectant.

A further aspect of the present invention comprises a moisturizing, personal cleansing composition comprising 2-40% oleosomes, 0.5-10% anionic surfactant, 3-30% non-ionic surfactant, 1-20% lipoaminoacidic surfactant, and 2-20% humectant to the keratinous tissue.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the personal cleansing composition alone, not accounting for the substrate weight. Each of the noted personal cleansing composition components and substrates is discussed in detail below.

The term "comprising", which is synonymous with "including," "containing," or "characterized by," is inclusive or open-ended and does not exclude additional, unrecited elements or method steps. See MPEP 2111.03. See, e.g., *Mars Inc. v. H.J. Heinz Co.*, 377 F.3d 1369, 1376, 71 USPQ2d 1837, 1843 (Fed. Cir. 2004) ("like the term 'comprising,' the terms 'containing' and 'mixture' are open-ended."). *Invitrogen Corp. v. Biocrest Mfg., L. P.*, 327 F.3d 1364, 1368, 66 USPQ2d 1631, 1634 (Fed. Cir. 2003) ("The transition 'comprising' in a method claim indicates that the claim is open-ended and allows for additional steps."); *Genentech, Inc. v. Chiron Corp.*, 112 F.3d 495, 501, 42 USPQ2d 1608, 1613 (Fed. Cir. 1997) See MPEP 2111.03. ("Comprising" is a term of art used in claim language which means that the named elements are essential, but other elements may be added and still form a construct within the scope of the claim.); *Moleculon Research Corp. v. CBS, Inc.*, 793 F.2d 1261, 229 USPQ 805 (Fed. Cir. 1986); *In re Baxter*, 656 F.2d 679, 686, 210 USPQ 795, 803 (CCPA 1981); *Ex parte Davis*, 80 USPQ 448, 450 (Bd. App. 1948). See MPEP 2111.03.

The term "consisting essentially of" as used herein, limits the scope of a claim to the specified materials or steps "and those that do not materially affect the basic and novel characteristic(s)" of the claimed invention. *In re Herz*, 537 F.2d 549, 551-52, 190 USPQ 461, 463 (CCPA 1976) (emphasis in original). See MPEP 2111.03.

The term "keratinous tissue" as used herein means skin, hair and nails.

The term "naturally-derived" as used herein is meant to mean that the ingredient comes or is made from a renewable resource found in nature (i.e., Flora, Fauna, Mineral). Petroleum compounds are expressly excluded from the term "naturally-derived".

The term "naturally-processed" as used herein is meant to mean the ingredients are processed using only ecologically-friendly processes. Ecologically-friendly processing is minimal processing that maximizes purity and minimizes negative effects on the ingredients. Only biodegradable reagents are used in ecologically-friendly processing. Naturally-processed as used herein includes at least distillation, condensation, extraction, steamed distillation, pressure cooking and hydrolysis.

Other examples of natural processes include: saponification which uses a strong alkali base (e.g., NaOH) to create a reaction with a fat or oil to produce soap, glycerine and water in one process; esterification and transesterification which involve reacting an alcohol and an acid or base to create safe emulsifiers, surfactants and solubalizers that thicken and hydrate moistuizers; and biofermentation which converts substances through the use of a yeast and/or a bacteria to produce nutrients and/or to purifiy formulations. The microorganisms do not survive the process.

Several processes dilute or change the composition of an ingredient to the point that an otherwise natural ingredient becomes "unnatural" by virtue of how it is processed. Ethoxylation, sulfination and polymerization processes are expressly excluded from the term "naturally-processed". For example, sulfonation uses harsh processing that involves sulfates, sulphonates and phosphates to create effective wetting agents for use in detergents and foaming agents. It is excluded from the definition of "naturally-processed" because sulfates do not break down in the environment. One example of a naturally derived synthetic substitute produced by processes such as sulfonation and ethoxylation is called sodium lauryl/laureth sulfate (SLS). SLS is derived from coconut oil, but is processed in such a way that does not render it an "eco-friendly, natural" ingredient as the term is used herein.

The term "safe" as used herein is meant to mean generally recognized as safe (GRAS) by Food and Drug Administration (FDA) when used in accordance with FDA's good manufacturing practices (GMP) and contain no residues of heavy metals or other contaminants in excess of tolerances set by FDA or EPA The term "biodegradable" as used herein is meant to mean microbial degradation of carbon containing materials. The "biodegradable" materials are tested under a recognized protocol and with tested methods of established regulatory bodies such as: EPA, EPA-TSCA, OECD, MITI or other similar or equivalent organizations in the US or internationally. Suitable non-limiting examples of test methods for biodegradation include: OECD methods in the 301-305 series. Generally, all "biodegradable" materials must meet the following limitations:

a) removal of dissolved organic carbon >70%
b) biological oxygen demand (BOD) >60%
c) % of BOD of theoretical oxygen demand >60%
d) % $CO_2$ evolution of theoretical >60%

The term "eco-friendly, natural composition" as used herein refers to compositions wherein at least 95% of the ingredients are naturally-derived, naturally-processed, safe, and biodegradable.

The term "eco-friendly, natural ingredient" refers to an ingredient that is naturally-derived, naturally-processed, safe and biodegradable.

The inventive moisturizing and cleansing compositions of the present invention contain at least 95% naturally-derived, naturally-processed, safe, biodegradable ingredients. Unlike prior art "natural" formulations, the compositions of the present invention have been shown to be as good or better than their synthetic or quasi-synthetic counterparts.

The outer layer of skin is made up of dead skin cells, natural oils and lipids (fats). It is designed by nature to protect your deeper layers of skin from irritants and toxins. Daily use of most cleansers can greatly reduce your skin's natural ability to repel the thousands of irritants and toxins that are commonly found in the home and work place. Once these irritants penetrate your outer layer of skin they can cause dry skin conditions, eczema, psoriasis, skin allergies and many other less desirable skin and health problems. Dry skin and itchy skin are nature's way of warning you that the protective elements of your outer layer of skin have been stripped away.

To reduce the risk of the potentially undesirable side effects associated with cleansers, a consumer-desirable attribute of a personal cleansing product is to provide both a cleansing benefit and a moisturizing benefit to the skin. However, one obstacle to providing these benefits is that the mechanisms behind them are diametrically opposed. To be effective, moisturizers need to adhere to the skin's surface. They are used to slow evaporation of the skin's moisture by replacing natural skin oils, covering tiny fissures in the skin and/or providing a protective film on the skin. Cleansers, on the other hand, tend to strip moisture along with dirt, oil and other contaminants away from the skin. Hence, finding the right combination to provide one product that achieves both cleansing and moisturizing is challenging on its own, and finding the right combination of eco-friendly, natural products presents an even greater challenge.

Several synthetic formulations exist which provide these benefits (e.g., Dove® Deep Moisture Beauty Body Wash, Ivory® Simplement Body Wash, Soft Soap® Moisture Body Wash), but until now no effective eco-friendly, natural formulation existed.

One challenge associated with avoiding synthetic ingredients or methods is finding suitable eco-friendly, natural ingredients that provide textures, lathers, creaminess, glossiness, rinsing, colors and fragrances that are equivalent to synthetic formulations. Product stability and shelf life are particularly challenging aspects of the process. Often synergistic interactions are discovered and embraced.

For example, when using eco-friendly, natural emulsifiers, it can be difficult to make sure that the product does not separate. Essential oils can sometimes cause base formulas to fail. Additionally, eco-friendly, natural preservatives in products are more delicate than synthetics and can break down with temperature changes during shipping. Compositions of the present invention are formulated to have shelf lives of at least 1 year and preferably at least 3 years.

Synthetic products that simultaneously moisturize and cleanse do so by removing dirt and distrupting the outer layer of oil, but then work to ensure the skin barrier is left intact by restoring the oil.

Dermatologists divide moisturizers into four different classes, based on how they work: occlusives, humectants, emollients and protein rejuvenators. Some moisturizers may fall within more than one of the four classes. Occlusives physically block water loss from the outermost layer of skin, the stratum corneum (SC). Some examples of occlusives include petrolatum, lanolin, mineral oil and silicones, such as dimethicone. Humectants attract water when applied to the skin and theoretically improve hydration of the SC. Some examples of humectants include propylene glycol, urea, glycerin and alphahydroxyacids, such as lactic acid and glycolic acid. Emollients smooth skin by positioning droplets of oil in the spaces between skin flakes. Emoillients are not usually occlusive. When combined with an emulsifier, they help hold oil and water in the SC. Examples of emoillients include mineral oil, lanolin, fatty acids, cholesterol, squalene, and structural lipids. Protein rejuvenators purport to rejuvenate the skin by replenishing essential proteins to it. Examples of rejuvenators include keratin and elastin.

In general, effective moisturizing involves a 4-step process: (1) repairing the skin barrier, (2) increasing water content to the SC, (3) reducing water loss from the SC, and (4) restoring the skin's ability to attract, hold and redistribute water.

One problem with traditional, eco-friendly natural skin moisturizers such as Aloe, Honey or Glycerin is that when formulated in combination with cleansers the moisturizer is stripped away during use.

Oleosomes

In the present invention, moisturizing is provided by oil-bodies or oleosomes. It has been found that all plant seeds that store triglycerides as future energy sources sequester these oils in specialized organelles called oil-bodies or oleosomes. In addition to being a future energy source, these oleosomes are natural reservoirs that function to preserve and protect seed oil from rancidity and oxidation. Oleosomes are spherical structures having an inner reservoir or core of triglycerides, surrounded by a phospholipid membrane or layer, which is encased or surrounded by unique proteins called oleosins.

The oleosins contain both hydrophilic and hydrophobic portions. Some of the hydrophobic portion penetrates into the triglyceride core and serves as an anchor, while the hydrophilic portion is free to solubilize in water. As will be discussed in more detail later, the hydrophilic-hydrophobic structure of the oleosomes enables them to be effective emulsifiers and their spherical orientation enables them to exhibit great efficiency as such.

Oleosomes are present in numerous plant seeds, e.g., rapeseed (*Brassica* spp.), soybean (*Glycine max*), sunflower (*Helianthus annuus*), oil palm (*Elaeis guineeis*), cottonseed (*Gossypium* spp.), groundnut (*Arachis hypogaea*), coconut (*Cocus nucifera*), castor (*Ricinus communis*), safflower (*Carthamus tinctorius*), mustard (*Brassica* spp. and *Sinapis alba*), coriander (*Coriandrum sativum*), squash (*Cucurbita maxima*), linseed/flax (*Linum usitatissimum*), Brazil nut (*Bertholletia excelsa*), jojoba (*Simmondsia chinensis*), cucumber (*Cucumis sativus*), maize (*Zea mays*), wheat and barley. Oil from these plants is typically obtained by pressing the seeds which ruptures the oleosomes and releases the oils. SemBioSys, Inc. has developed a method to isolate and wash the intact plant oleosomes. This method is disclosed in U.S. Pat. Nos. 6,146,645, 6,599,513 and 6,582,710, which are all hereby incorporated by reference in their entirety. Isolating and washing the oil bodies removes significant amounts of seed contaminants such as proteins, volatiles and other compounds which may impart undesirable color, odor, organoleptic characteristics, allergenic characteristics or other undesirable characteristics. As used herein the terms "oil bodies" and "oleosomes" refer to intact plant oleosomes as just described.

Safflower, sunflower, linseed, and canola seeds are good examples of seeds having a high triglyceride content. Isolated intact oleosomes from plants, such as safflower can be obtained from Botaneco, Bensalem, Pa. Safflower oleosomes from Botaneco are 100% naturally-processed using a proprietary process that does not involve the use of emulsifiers or solvents of any kind. The oleosomes are sold under the tradename Hydresia™ and have the following characteristics: Particle Size 1-3 uM; pH range 4.0-8.0; Oleosome content 55-78%; Protein content 0.3-0.9%; Vitamin E (α-Tocopherol) content 60 mg/100 g of oil bodies.

The inventors have found that embodiments of the present invention in practice result in compositions that deposit oleosomes on the skin and that the oleosomes remain on the skin even after the cleansing reagents are washed away. In addition to remaining on the skin, the inventors have found that the oleosomes actually provide prolonged moisturizing benefits because the outer membrane slowly breaks over time resulting in time-released tryglycerides which soften and protect the skin, serving both as an emoillient and an occlusive. Compositions of the present invention can contain oleosomes in an amount ranging between 2-40%, with preferred amounts ranging between 5-20%.

Humectants

Humectants are hygroscopic substances that help the skin retain moisture. Humectants soften and soothe the skin and derive their moisturizing abilities from water which they pull from the nearest available source.

Examples of commonly used humectants include Propylene Glycol, Mineral Oil, Polyethylene Glycol, and Urea. A humectant like mineral oil, however, can actually build up under the skin and prevent the skin from absorbing essential vitamins and nutrients. Many vegetable oils which do not deprive the skin of vitamins and nutrients can be used in place of mineral oil. Examples of eco-friendly, natural humectants include glycerin, lecithin, and honey.

A preferred eco-friendly, natural humectant is glycerine. Glycerin is a neutral, thick liquid which freezes to a gummy paste and which has a high boiling point. Glycerin can be dissolved into water or alcohol, but not oils. On the other hand, many things will dissolve into glycerin easier than they do into water or alcohol. So it is a good solvent. For example, glycerine can be used to solublize ingredients, such as a thickener like xanthan gum. Compositions of the present invention can contain humectants in an amont ranging between 2-20%, with preferred amounts ranging between 3-15%.

Surfactants

In the compositions of the present invention, cleansing is provided by surfactants. A surfactant or surface active agent is a substance that, when dissolved in water, gives a product the ability to remove dirt, sweat, sebum, and oils from the human skin. Surfactants enable the product to fully wet the skin so that environmental dirt and body secretions can be readily loosened and removed. Skin cleansing is quite a complex process. An ideal cleanser should remove dirt effectively without causing irritation or damage to the skin. Surfactants enable oily dirt, which normally does not dissolve in water, to become dispersible in water and rinsed away. Each surfactant molecule has a hydrophilic head that is attracted to water molecules and a hydrophobic tail that repels water and bonds itself to the oily dirt.

Surfactants can also be referred to as wetting agents and foamers because they lower the surface tension of the medium in which it is dissolved. By lowering this interfacial tension between two media or interfaces (e.g., skin/water) the surfactant plays a key role in the removal and suspension of dirt and oil. The lower surface tension of the water makes it easier to lift dirt and grease off of the skin. As the hydrophilic head remains in the water, it pulls the dirt and oil that is bonded to the hydrophobic tail away from the skin and into the water. However, many surfactants can also have the following harmful effects on the skin: after-wash tightness (AWT), dryness, damage to the barrier function of the skin, redness, irritation and itching.

It is believed that surfactants irritate the skin by interacting with the skin's natural proteins, such as corneocytes. Corneocytes are protein complexes made of threads of keratin in an organized matrix. The surfactants bind to these proteins allowing them to become over-hydrated and swell. This swelling can make it easier for the cleanser ingredients to penetrate into the lower layers of the skin where they can interact with the nerve endings and immune system, possibly causing itching and irritation. Thus, personal cleansers that contain only eco-friendly, natural ingredients are highly desirable to eliminate these potential ill-effects primarily associated with synthetic cleanser ingredients.

The compositions of the present invention provide mild, eco-friendly, natural surfactants that comprise a combination of an anionic surfactant, a non-ionic surfactant and a lipoamino acid surfactant. In solution, anionic surfactants have a negatively charged head. They are particularly effective at oily soil cleaning, but they can react with the positively charged ions (calcium and magnesium) in hard water, which can lead to partial deactivation.

Anionic surfactants suitable for use in the compositions of the present invention include sodium stearoyl lactylate, sodium lauroyl lactylate, and alkylpolyglucosides such as coco glucoside. A preferred anionic surfactant is coco-glucoside which is derived from coconut oil and fruit sugar. Coco-glucoside enables loose foaming and enhanced viscosity, particularly if used in conjunction with a compound such as glyceryl oleate. Glyceryl oleate which is derived from glycerin and oleic acid functions as an emoillient and a thickener. Used alone, coco-glucoside provides cleansing. Used in conjunction with glyceryl oleate, the combination of coco-glucoside and glyceryl oleate provides cleansing and enhanced moisturization.

Coco-glucoside together with glyceryl oleate may be obtained from Cognis Corporation, Ambler, Pa. under the tradename Lamesoft® PO65. Compositions of the present invention can contain anionic surfactants in amounts ranging between 0.5-10%, with preferred amounts ranging between 1-5%. Additional emoillients such as glyceryl oleate can be present in amounts ranging from between 0.25-10%, with preferred amounts ranging between 0.25-5%.

Non-ionic surfactants do not have an electrical charge, which makes them resistant to water hardness deactivation. They are excellent oil removers and are often used together with anionic surfactants because contribute to making the surfactant system less hardness sensitive.

Non-ionic surfactants suitable for use in the compositions of the present invention include, for example, sucrose stearate, sucrose laurate, sucrose palmitate, lauryl glucoside, caprylyl/capryl glucoside, inulin lauryl carbamate, decyl glucoside. A preferred non-ionic surfactant is decyl glucoside which like coco-glucoside also enables loose foaming and enhanced viscosity. Decyl glucoside is produced by the reaction of glucose from corn starch with the fatty alcohol decanol which is derived from coconut. Decyl glucoside may be obtained from Cognis Corporation, Ambler, Pa. Compositions of the present invention can contain non-ionic surfactants in an amont ranging between 3-30%, with preferred amounts ranging between 10-25%.

Lipoamino acid surfactants provide an alternative to traditional surfactants. Lipoamino acids comprise a fatty acid component (lipophilic/hydrophobic portion) and an amino acid component (hydrophilic portion). All have been found to be highly biodegradable, with low toxicity, ecotoxicity and irritation effects. Foaming polypeptides are a form of lipoamino acid surfactants that are highly functional fatty acid derivatives of hydrolyzed proteins and amino acids. Foming polypeptides are prepared by reacting hydrolyzed protein with a reactive fatty acid reagent. The fatty acid group is covalently bonded to the polypeptide chain as a result of the reaction. Once the carboxylic acid group is neutralized, a soluble foaming polypeptide is formed.

Lipoamino acid surfactants suitable for use in the compositions of the present invention include sodium cocoyl hydrolyzed wheat protein and sodium cocyl hydrolyzed soy protein. A preferred lipoamino acid is sodium cocyl hydrolyzed soy protein or Foam-Soy C obtained from Arch Personal Care Products, South Plainfield, N.J. Lipoamino acid surfactants provide mild cleansing and a rich lather. Compositions of the present invention can contain lipoamino acid surfactants in an amont ranging between 1-20%, with preferred amounts ranging between 2-10%.

Emulsifiers

An emulsifier is a substance which stabilizes an emulsion. Surfactants are frequently used as emulsifiers in personal care products. Examples of commonly used emulsifier are fatty esters, silicones, polymers, and ethoxylates. Emulsifiers typically have a hydrophobic (water-hating) and a hydrophilic (water-liking) end. In oil-in-water emulsions, the emulsifiers will surround an oil (or other immiscible molecule) and form a protective layer so that the oil molecules cannot "clump" together. This action helps keep the dispersed phase in small droplets and preserves the emulsion.

As previously discussed, oleosomes have an inner reservoir of triglycerides that are surrounded by a phospholipid membrane that is encased by proteins called oleosins. The oleosins contain both hydrophilic and hydrophobic portions which make them great emulsifiers. The preferred emulsifiers for the compositions of the present invention are the oleosomes themselves.

Another advantage of using the oleosomes as the emulsifier is that the manufacturing process can be simplified. With traditional emulsifiers, heat and high Sheer mixing is required. Use of the oleosomes eliminates the need to heat and allows the emulsification to be conducted as a cold process.

In the compositions of the present invention, the oleosomes serve a dual purpose; they act as both a moisturizer and an emulsifier, thus eliminating the need for additional emulsifiers in the compositions. The oleosomes can be the only emulsifier present in the compositions of the present invention or they can be used in tandem with other suitable emulsifiers. Other suitable emulsifiers include those known to those skilled in the art. For example, sucrose stearate, sodium stearate, glyceryl oleate, and cetyl alcohol. Compositions of the present invention can contain emulsifiers other than oleosomes in an amont ranging between 0.5-30%, with preferred amounts ranging between 2-10%.

Optional Ingredients

Compositions of the present invention may contain the following optional ingredients: preservatives, emoillients, vitamins, plant extracts, exfoliants, fragrances, colorants, royal jelly and any other ingredients generally known to those skilled in the art. For example, glyceryl oleate is particularly effective when combined with the anionic surfactant coco-glucoside as previously discussed. Compositions of the present invention can contain optional ingredients in an amont ranging between 0.001-20%, with preferred amounts ranging between 0.5-10%.

Preservative System

Compositions of the present invention can be shelf stable for up to six months, more preferably up to one year and most preferably up to three years using a naturally-derived, naturally-processed, safe, and biodegradable preservative system. One suitable preservative system comprises an enzyme-based oxygen scavenging antioxidant system as described in U.S. Pat. No. 5,972,355 which is hereby incorporated by reference in its entirety. The combination of glucose, glucose oxidase and lactoperoxidase is one example of an enzyme-based oxygen scavenging antioxidant system. The combination of glucose, glucose oxidase and lactoperoxidase is available as Biovert® from Arch Personal Care Products, South Planfield, N.J. The total of all components in a preservative system may be present in amonts ranging from 0.1-5% and preferably in amounts ranging from 0.25-1.5%.

Although less desirable than an eco-friendly, natural preservative or preservative system, because such small amounts are necessary to be effective, synthetic preservatives such as Methyl, Ethyl. Propyl and Butyl Parabens, Methylisothiazolinone, Methylchloroisothazolinone, Isobutyl Paraben, and DMDM Hydantoin are also suitable for use with the present invention.

Exfoliants

Exfoliants break down and remove keratinized cells that naturally build up on the skin's surface. Even skin functioning at peak performance and normal skin can benefit from an exfoliant. Exfoliants help restore a healthy, translucent glow many consumers strive for. Suitable eco-friendly, natural exfoliants include fruit seeds and fibers, grain powders, nut/seed meal, oil/wax beads, sugar and jojoba beads. Exfoliants are typically present in amonts ranging from 0.01-10% and preferably in amounts ranging from 0.1-10%.

Fragrances and Essential Oils

Fragrances and essential oils are often added to personal care compositions in small amounts to provide an aromatically pleasing effect. Suitable eco-friendly, natural fragrances and essential oils include those generally known to one skilled in the art. For example, citrus essential oils and floral essential oils.

Thickeners

Thickeners are sometimes added to personal care compositions to enhance the viscosity of the composition, and to stabilize emulsions. Suitable eco-friendly, natural thickeners include those generally known to one skilled in the art. For example, xanthan gum, carrageenan, gum arabic. Thickeners are typically present in amonts ranging from 0.05-2% and preferably in amounts ranging from 0.1-1%.

Preferred characteristics of a final formulation include an attractive appearance and color (e.g., creamy white to off-white), a pH in the range of 4.5-6.5, a viscosity in the range of 1,000-10,000 cps (Brookfield RVT; spindle 4 @ 20 rpms), and specific gravity in the range of 0.990-1.100.

EXAMPLES

The personal, cleansing compositions of the present invention are high performing, eco-friendly, natural, formulations with a minimum of essential eco-friendly, natural ingredients. Competitive personal, cleansing products are either natural and inferior in performance or contain additional ingredients that make them non-natural, such as synthetic components.

Two embodiments of eco-friendly, natural compositions of the present invention were prepared. Formulation A comprises: Water, decyl glucoside, *carthamus tinctorius* (safflower) oleosomes, sodium cocoyl hydrolyzed soy protein, glycerin, coco-glucoside, glyceryl oleate, fragrance, royal jelly, simmondsia chinensis (jojoba) oil, hydrogenated jojoba oil, *vaccinium myrtillus* (bilberry) extract, saccharum officinarum (sugar cane) extract, *acer saccharinum* (sugar maple) extract, citrus aurantium dulcis (orange) fruit extract, citrus medica limonum (lemon) extract, glucose, xanthan gum, citric acid, sodium chloride, lactoperoxidase, glucose oxidase. Formulation A is a white to off-white liquid; pH 5.5-6.5, an initial viscosity 2500-3100 cp and a final viscosity (24 hours after initial reading) of 2700-3300 cps (Brookfield RVT viscometer; spindle 4 @ 20 rpms).

Formulation B comprises: Water, decyl glucoside, *carthamus tinctorius* (safflower) oleosomes, sodium cocoyl hydrolyzed soy protein, glycerin, fragrance, coco-glucoside, glyceryl oleate, non-fat dry milk, butyrospermum parkii (shea butter), xanthan gum, glucose, citric acid, glucose oxidase, and lactoperoxidase. Formulation B is a white to off-white liquid; pH 5.5-6.5, an initial viscosity 2500-3100 cps and a final viscosity (24 hours after initial reading) of 2600-3300 cps (Brookfield RVT viscometer; spindle 4 @ 20 rpms).

Formulation B was compared with a leading moisturizing cleanser, Dove® Deep Moisture Beauty Body Wash, which contains primarily synthetic active ingredients, hereinafter referred to as the Synthetic Formulation. According to the label, the Synthetic Formulation comprises: Water, Glycine Soja (Soybean) Oil or *Helianthus Annuus* (Sunflower) Seed Oil, Glycerin, Petrolatum, Ammonium Lauryl Sulfate, Cocamidopropyl Betaine, Ammonium Laureth Sulfate, Lauric Acid, Cocamide MEA, Fragrance, Polybutene or Polyisobutylene, Guar Hydroxypropyltrimonium Chloride, Isostearic Acid, PEG-5 Cocamide, Acrylates/Beheneth-25 Methacrylate Copolymer PEG-30 Dipolyhydroxystearate, DMDM Hydantoin, Tetrasodium EDTA, Etidronic Acid, Iodopropynyl Butylcarbamate, and Titanium Dioxide (CI-77891).

Twenty-four female panelists ranging in age from 34-61 participated in a two week study. Baseline Corneometer evaluations were recorded for all participants on the volar surface of the right and left forearm of each participant. Immediately following the baseline Corneometer evaluations, approximately 0.5 ml of Formulation B and the Synthetic Formulation were applied to the volar surface of the right and left forearm of each participant and immediate post-treatment Corneometer readings were recorded. Participants then used each product for one week.

Tables 1A and 1B list the average Corneometer measurements and calculated percentage changes from baseline for each participant immediate post-treatment and after one week of use. Tables 2A and 2B include the statistical comparison of Corneometer readings between baseline, immediate post-treatment and after one week of use.

The study found that for sites treated with Formulation B, statistically significant ($p<0.05$) increases in skin surface hydration were measured immediately post-application (54%) and following one week of treatment (15%) compared to baseline. For sites treated with the Synthetic Formulation, statistically significant increases in skin surface hydration were measured immediately post-application (61%) compared to baseline, although no significant differences in skin surface hydration were measured following one week of treatment.

Additionally, the study found that immediately following treatment and after one week of product use, skin surface hydration levels were statistically the same for Formulation B and the Synthetic Formulation.

TABLE 1A

Formulation B

| | Skin Hydration | | | % Change from Baseline | |
|---|---|---|---|---|---|
| Participant | Baseline | Immediate | Week 1 | Immediate | Week 1 |
| 1 | 59 | 80 | 58 | 36% | -2% |
| 2 | 35 | 56 | 39 | 60% | 11% |
| 3 | 46 | 59 | 54 | 28% | 17% |
| 4 | 45 | 76 | 56 | 69% | 24% |
| 5 | 47 | 83 | 51 | 77% | 9% |
| 6 | 58 | 90 | 63 | 55% | 9% |
| 7 | 49 | 84 | 68 | 71% | 39% |
| 8 | 49 | 73 | 64 | 49% | 31% |
| 9 | 37 | 104 | 50 | 181% | 35% |
| 10 | 50 | 73 | 62 | 46% | 24% |
| 11 | 62 | 65 | 66 | 5% | 6% |
| 12 | 46 | 71 | 44 | 54% | -4% |
| 13 | 64 | 87 | 68 | 36% | 6% |
| 14 | 51 | 85 | 46 | 67% | -10% |
| 15 | 46 | 78 | 45 | 70% | -2% |
| 16 | 35 | 55 | 41 | 57% | 17% |
| 17 | 42 | 68 | 60 | 62% | 43% |
| 18 | 48 | 63 | 48 | 31% | 0% |
| 19 | 54 | 74 | 50 | 37% | -7% |
| 20 | 48 | 67 | 58 | 40% | 21% |
| 21 | 44 | 78 | 57 | 77% | 30% |
| 22 | 45 | 68 | 40 | 51% | -11% |
| 23 | 60 | 64 | 69 | 7% | 15% |
| 24 | 45 | 59 | 72 | 31% | 60% |
| Mean | 49 | 73 | 55 | 54% | 15% |
| Std. Dev. | 8 | 12 | 10 | 33% | 18% |

TABLE 1B

Synthetic Formulation

| | Skin Hydration | | | % Change from Baseline | |
|---|---|---|---|---|---|
| Participant | Baseline | Immediate | Week 1 | Immediate | Week 1 |
| 1 | 60 | 71 | 69 | 18% | 15% |
| 2 | 38 | 86 | 32 | 126% | -16% |
| 3 | 50 | 69 | 52 | 38% | 4% |
| 4 | 42 | 64 | 49 | 52% | 17% |
| 5 | 52 | 103 | 57 | 98% | 10% |
| 6 | 53 | 81 | 62 | 53% | 17% |
| 7 | 46 | 92 | 63 | 100% | 37% |
| 8 | 42 | 94 | 70 | 124% | 67% |
| 9 | 41 | 72 | 51 | 76% | 24% |
| 10 | 51 | 93 | 63 | 82% | 24% |
| 11 | 65 | 96 | 67 | 48% | 3% |
| 12 | 48 | 60 | 43 | 25% | -10% |
| 13 | 60 | 78 | 55 | 30% | -8% |
| 14 | 49 | 63 | 42 | 29% | -14% |
| 15 | 44 | 92 | 35 | 109% | -20% |
| 16 | 38 | 57 | 42 | 50% | 11% |
| 17 | 42 | 72 | 51 | 71% | 21% |
| 18 | 50 | 66 | 36 | 32% | -28% |
| 19 | 51 | 64 | 49 | 25% | -4% |
| 20 | 50 | 70 | 57 | 40% | 14% |
| 21 | 50 | 106 | 59 | 112% | 18% |
| 22 | 45 | 64 | 53 | 42% | 18% |
| 23 | 56 | 68 | 73 | 21% | 30% |
| 24 | 58 | 92 | 66 | 59% | 14% |
| Mean | 49 | 73 | 54 | 61% | 10% |
| Std. Dev. | 7 | 15 | 12 | 35% | 21% |

TABLE 2A

Dunnett's Test
Comparison of Corneometer Readings between Baseline and Post-Application Intervals

| | Mean | | | |
|---|---|---|---|---|
| Formulation | Baseline | Immediate | Week 1 | P-Value of ANOVA Test |
| Formulation B | 49 | 73 | 55 | <0.0001* (Baseline vs. Immediate Baseline vs. Week 1) |
| Synthetic Formulation | 49 | 78 | 54 | <0.0001* (Baseline vs. Immediate |

*Statistically Significant

TABLE 2B

Paired t-Test
Comparison of Percent Changes in Corneometer Readings from Baseline between Formulation B and the Synthetic Formulation at Immediate Post-Treatment and Week 1

| | Mean of Percent Change From Baseline | | |
|---|---|---|---|
| Time Interval | Formulation B | Synthetic Formulation | P-Value of Paired t-Test |
| Immediate | 54% | 61% | 0.3775 |
| Week 1 | 15% | 10% | 0.1967 |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A moisturizing, personal cleansing composition comprising:
   (a) a plurality of *carthamus tinctorius* (safflower) oleosomes;
   (b) an anionic surfactant selected from the group consisting coco-glucoside, sodium stearoyl lactylate, sodium lauryl lactylate;
   (c) a non-ionic surfactant selected from the group consisting of lauryl glucoside, caprylyl/capryl glucoside, inulin lauryl carbamate, decyl-glucoside;
   (d) a lipoaminoacidic surfactant selected from the group consisting of sodium cocoyl hydrolyzed soy protein and sodium cocoyl hydrolyzed wheat protein; and
   (e) a humectant selected from the group consisting of glycerine, lecithin and honey;
   wherein (a)-(e) are naturally-derived, naturally-processed, safe, and biodegradable; and
   wherein the topical application of the composition to keratinous tissue cleanses and moisturizes the tissue.

2. The moisturizing, personal cleansing composition recited in claim 1, wherein
   the oleosomes are present in amounts ranging from 2-40%;
   the anionic surfactant is present in amounts ranging from 0.5-10%;
   the non-ionic surfactant is present in amounts ranging from 3-30%;
   the lipoaminoacidic surfactant is present in amounts ranging from 1-20%; and
   the humectant is present in amounts ranging from 2-20%.

3. The moisturizing, personal cleansing composition recited in claim 1, wherein the viscosity of the composition is between 1,000-10,000 cps.

4. The moisturizing, personal cleansing composition recited in claim 1, wherein the pH is between 4.5 and 6.5.

5. The moisturizing, personal cleansing composition recited in claim 1, having a moisturizing performance comparable to that of a synthetic formulation.

6. The moisturizing, personal cleansing composition recited in claim 1, having a skin moisturizing performance that increases the skin surface hydration immediately after application as measured using a Corneometer by at least 5%.

7. A moisturizing, personal cleansing composition comprising:
   (a) a plurality of *carthamus tinctorius* (safflower) oleosomes;
   (b) an anionic surfactant selected from the group consisting coco-glucoside, sodium stearoyl lactylate, sodium lauryl lactylate;
   (c) a non-ionic surfactant selected from the group consisting of lauryl glucoside, caprylyl/capryl glucoside, inulin lauryl carbamate, decyl-glucoside;
   (d) a lipoaminoacidic surfactant selected from the group consisting of sodium cocoyl hydrolyzed soy protein and sodium cocoyl hydrolyzed wheat protein;
   (e) a humectant selected from the group consisting of glycerine, lecithin and honey; and
   (f) 0.25-1.5% by weight of a preservative system comprising an enzyme-based oxygen scavenging antioxidant system
   wherein (a)-(f) are naturally-derived, naturally-processed, safe, and biodegradable; and
   wherein the topical application of the composition to keratinous tissue cleanses and moisturizes the tissue.

8. The moisturizing, personal cleansing composition recited in claim 7, wherein the cleansing composition is shelf stable for up to one year.

9. The moisturizing, personal cleansing composition recited in claim 7, wherein the cleansing composition is shelf stable for up to three years.

10. The moisturizing, personal cleansing composition recited in claim 7, wherein the enzyme-based oxygen scavenging antioxidant system is glucose, glucose oxidase, and lactoperoxidase.

11. The moisturizing, personal cleansing composition recited in claim 10, wherein the cleansing composition is shelf stable for up to one year.

12. The moisturizing, personal cleansing composition recited in claim 1, further comprising at least one additional component comprising:
   an emulsifier;
   an emoillient;
   an exfoliant;
   a fragrance;
   an essential oil;
   a vitamin;
   a plant extract;
   a colorant;
   a thickener; and
   royal jelly.

13. The moisturizing, personal cleansing composition recited in claim 12, wherein the at least one additional component is naturally-derived, naturally-processed, safe, and biodegradable.

14. The moisturizing, personal cleansing composition recited in claim 1, further comprising an emollient and the emollient is glyceryl oleate.

15. The moisturizing, personal cleansing composition recited in claim 1, having a skin moisturizing performance that increases the skin surface hydration by at least 15% with regular use for at least one week as measured using a Corneometer.

16. A method of cleansing and moisturizing keratinous tissue comprising:
   topically applying a composition comprising:
      (a) a plurality of naturally-derived, naturally-processed, safe, and biodegradable *carthamus tinctorius* (safflower) oleosomes;
      (b) an naturally-derived, naturally-processed, safe, and biodegradable anionic surfactant selected from the group consisting coco-glucoside, sodium stearoyl lactylate, sodium lauryl lactylate;
      (c) a naturally-derived, naturally-processed, safe, and biodegradable non-ionic surfactant selected from the group consisting of lauryl glucoside, caprylyl/capryl glucoside, inulin lauryl carbamate, decyl-glucoside;
      (d) a naturally-derived, naturally-processed, safe, and biodegradable lipoaminoacidic surfactant selected from the group consisting of sodium cocoyl hydrolyzed soy protein and sodium cocoyl hydrolyzed wheat protein; and
      (e) a naturally-derived, naturally-processed, safe, and biodegradable humectant selected from the group consisting of glycerine, lecithin and honey;
   to keratinous tissue to cleanse and moisturize the keratinous tissue.

17. The method recited in claim 16, further comprising the step of:
   rinsing the keratinous tissue with water after topically applying the composition to the keratinous tissue.

* * * * *